(12) United States Patent
Holy et al.

(10) Patent No.: US 6,379,962 B1
(45) Date of Patent: Apr. 30, 2002

(54) POLYMER SCAFFOLD HAVING MICROPOROUS POLYMER STRUTS DEFINING INTERCONNECTED MACROPORES

(75) Inventors: Chantal E. Holy; Molly S. Shoichet; John E. Davies, all of Toronto (CA)

(73) Assignee: Bonetec Corporation, Toronto (CA)

( * ) Notice: Subject to any disclaimer, the term of this patent is extended or adjusted under 35 U.S.C. 154(b) by 0 days.

(21) Appl. No.: 09/191,107

(22) Filed: Nov. 13, 1998

(30) Foreign Application Priority Data

Nov. 14, 1997 (CA) .............................................. 2221195

(51) Int. Cl.[7] .......................... C12N 5/06; C12N 5/08; C12N 11/08; A61F 2/00
(52) U.S. Cl. ...................... 435/395; 424/39.7; 424/423; 435/180; 435/396; 435/402
(58) Field of Search .............................. 424/93.7, 423; 435/174, 180, 182, 395, 396, 402

(56) References Cited

U.S. PATENT DOCUMENTS

| 5,041,138 A |   | 8/1991 | Vacanti et al. ................. 623/16 |
| 5,228,994 A | * | 7/1993 | Tkacik et al. .......... 210/500.29 |
| 5,338,772 A |   | 8/1994 | Bauer et al. ................. 523/115 |
| 5,498,335 A | * | 3/1996 | Moya ......................... 210/490 |
| 5,514,378 A |   | 5/1996 | Mikos et al. ................ 424/425 |

FOREIGN PATENT DOCUMENTS

EP 0747068 12/1996

OTHER PUBLICATIONS

"Porosity and Specific Surface of Bone" by Martin RB in CRC Critical Reviews in Biomedical Engineering, 10(3), 179–22, 1984.

K. Whang et al., "A Novel Method to Fabricate Bioabsorbable Scaffolds", *Polymer*, Vol. 36, No. 4, pp. 837–842, 1995 Elsevier Science Ltd.

Mooney et al., "Novel Approach to Fabricate Porous Sponges of Poly (D,L–Lactic–co–glycolic acid) Without the Use of Organic Solvents", *Biomaterials*, vol. 17, pp. 1417–1422, 1996 Elsevier Science Ltd.

Thomson et al., "Fabrication of Biodegradable Polymer Scaffolds to Engineer Trabecular Bone", *J. Biomater. Sci. Polymer Edn.*, Vol. 7, No. 1, pp. 23–38, 1995 VSP.

Mikos et al., "Laminated Three–Dimensional Biodegradable Foams for Use in Tissue Engineering", *Biomaterials*, Vol. 14, No. 5, pp. 323–330, 1993 Butterworth–Heinemann Ltd.

Schugens et al., "Polylactide Macroporous Biodegradable Implants for Cell Transplantation. II. Preparation of Polylactide Foams by Liquid—Liquid Phase Separation", *Journal of Biomedical Materials Research*, Vol. 30, pp. 449–461, 1996 John Wiley & Sons.

Ishaug–Riley et al., "Three–Dimensional Culture of Rat Calvarial Osteoblasts in Porous Biodegradable Polymers", *Biomaterials*, Vol. 19, pp. 1405–1412, 1998 Elsevier Science Ltd.

Ishaug et al., "Bone Formation by Three–Dimensional Stromal Osteoblast Culture in Biodegradable Polymer Scaffolds", *Journal of Biomedical Materials Research*, vol. 36, pp. 17–28, 1997 John Wiley & Sons, Inc.

* cited by examiner

*Primary Examiner*—David M. Naff
(74) *Attorney, Agent, or Firm*—Lynn C. Schumacher; Hill & Schumacher

(57) ABSTRACT

A polymer scaffold is provided having an extensively interconnected macroporous network with macropores having microporous struts as walls. Macropore diameter ranges from about 0.5 to about 3.5 mm. The polymer may be a biocompatible, biodegradable polymer such as poly(lactide-co-glycolide) containing 75% polylactide and 25% polyglycolide. The polymer scaffold is prepared by mixing a liquid polymer with particles, precipitating the liquid polymer with a non-solvent for the liquid polymer and dissolving the particles with a solvent to form the macroporous polymer scaffold which preferably has porosity greater than 50%. The surface of the polymer scaffold may be modified by acid or base treatment, or by collagen or calcium phosphate deposition. The polymer scaffold has utility for tissue engineering, particularly as a scaffold for in vitro and in vivo cell growth.

16 Claims, 15 Drawing Sheets

POLYMER SCAFFOLD HAVING MICROPOROUS POLYMER STRUTS DEFINING INTERCONNECTED MACROPORES

FIELD OF THE INVENTION

The present invention relates to the use of a biodegradable polymer scaffold for tissue engineering applications. More particularly, the present invention relates to a novel macroporous polymer scaffold having a high level of interconnectivity between macropores.

BACKGROUND OF THE INVENTION

Bone treatments for injuries, genetic malformations and diseases often require implantation of grafts. It is well known that autografts and allografts are the safest implants; however, due to the limited supply and the risks of disease transmission and rejection encountered with these grafts, synthetic biomaterials have also been widely used as implants. Complications in vivo were observed with some of these biomaterials, as mechanical mismatches (stress shielding) and appearance of wear debris lead to bone atrophy, osteoporosis or osteolysis around the implants (Woo et al., 1976; Terlesen et al., 1988).

A new approach, defined as Tissue Engineering (TE), has recently raised a lot of interest. Tissue engineering involves the development of a new generation of biomaterials capable of specific interactions with biological tissues to yield functional tissue equivalents. The underlying concept is that cells can be isolated from a patient, expanded in cell culture and seeded onto a scaffold prepared from a specific biomaterial to form a scaffold/biological composite called a "TE construct". The construct can then be grafted into the same patient to function as a replacement tissue. Some such systems are useful for organ tissue replacement where there is a limited availability of donor organs or where, in some cases (e.g. young patients) inadequate natural replacements are available. The scaffold itself may act as a delivery vehicle for biologically active moieties from growth factors, genes and drugs. This revolutionary approach to surgery has extensive applications with benefits to both patient well-being and the advancement of health care systems.

The application of tissue engineering to the growth of bone tissue involves harvesting osteogenic stem cells, seeding them and allowing them to grow to produce a new tissue in vitro. The newly obtained tissue can then be used as an autograft. Biodegradable polyesters—in particular poly (lactide-co-glycolide)s—have been used as scaffolds for tissue engineering of several different cell populations, for example: chondrocytes (as described by Freed et al. in the J. of Biomed. Mater. Res. 27:11–13, 1993), hepatocytes (as described by Mooney et al. in the Journal of Biomedical Mat. Res. 29, 959–965, 1995) and most recently, bone marrow-derived cells (as described by Ishaug et al in the J. Biomed. Mat. Res. 36: 17–28, 1997 and Holy et al., in Cells and Materials, 7, 223–234, 1997). Specifically, porous structures of these polyesters were prepared and seeded with cells; however, when bone marrow-derived cells were cultured on these porous structures, bone Ingrowth only occurred within the outer edge of 3-D polymeric scaffold (Ishaug et al, supra; Holy et al., supra). Thus, the polymeric scaffolds prepared in these instances were inadequate to allow for the cell growth required to render tissue suitable for implantation or for use as an autograft.

SUMMARY OF THE INVENTION

It has now been found that polymer scaffolds characterized by macropores in the millimeter size range with inter-connections as seen in trabecular bone, are particularly useful for tissue engineering as they allow cell ingrowth which is crucial for the development of three-dimensional tissue. Such polymer scaffolds can be prepared using a novel process which combines the techniques of phase-inversion and particulate-leaching.

Accordingly, in one aspect of the present invention, there is provided a polymer scaffold comprising macropores, ranging in size between 0.5 mm to 3.5 mm, and having an interconnecting porosity similar to that found in human trabecular bone.

More particularly, the present invention provides a macroporous polymer scaffold with a trabecular morphology having a porosity of at least 50% and including polymer struts forming pore walls defining macropores which have a mean diameter in a range from about 0.5 to about 3.5 mm and are interconnected by macroporous passageways.

In one aspect of the invention there is provided a process for synthesizng a macroporous polymer scaffold with microporous polymer struts defining interconnected macropores, comprising the steps of:

mixing liquid polymer with particles to form a mixture of the liquid polymer and particles;

submerging the mixture in a non-solvent for the liquid polymer to precipitate said liquidpolymer producing a solidified mixture; and submerging the solidified mixture into a solvent that dissolves the particles for a time sufficient to dissolve the particles to obtain said macroporous polymer scaffold with microporous polymer struts defining interconnected macropores.

In another aspect of the invention there is provided a macroporous polymer scaffold with microporous polymer struts defining interconnected macropores formed by mixing liquid polymer with particles to form a mixture of the liquid polymer and particles, submerging the mixture in a non-solvent for the liquid polymer to precipitate the liquid polymer to produce a solidified mixture, and submerging the solidified mixture into a solvent that dissolves, the particles for a time sufficient to dissolve the particles to obtain said macroporous polymer scaffold with microporous polymer struts defining interconnected macropores.

BRIEF DESCRIPTION OF THE DRAWINGS

Embodiments of the present invention are described in greater detail with reference to the accompanying drawings and computer digitized micrographs, in which.

DETAILED DESCRIPTION OF THE INVENTION

Figure 1:
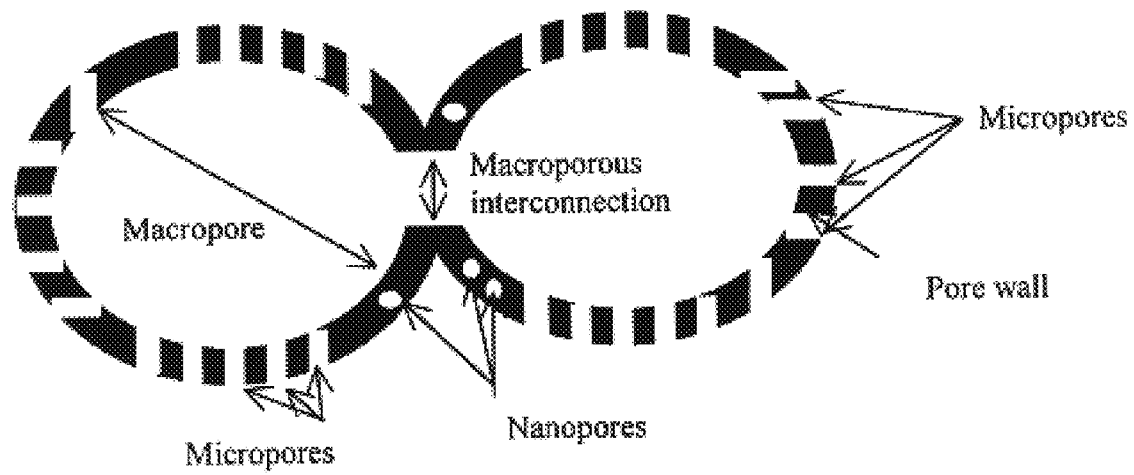
FIG. 1 is a diagrammatic representation of a portion of a polymer pore system illustrating different components as defined hereinafter.

FIG. 1 is a diagrammatic representation of a portion of a polymer scaffold showing two macropores interconnected with each other by a macroporous interconnection. The two macropores are also connected to the surrounding macropores by microporous passageways (also referred to as micropores). These and several other terms used in the description of the polymer scaffold produced according to the present invention are defined herebelow.

Scaffold: device designed as a cell carrier for tissue engineering or related applications. This device has preferably a porous morphology to be colonized by cells. In our specific case, the scaffold has an open-pore morphology.

Macropores: voids within the polymer scaffold, delinated by polymer walls. The macropores typically have a diameter between 0.5 and 3.5 mm.

Pore walls: polymer struts that delineate macropores. When the polymer struts form anisotropic bundles, in which microporous interconnections separate struts from each other in the same bundle, the structure of the pore wall is defined as "lamellar". The struts may also exhibit isotropic morphologies in which the struts and are widely separated from each other by mostly macroporous interconnections, Both lamellar and strut-like pore wall structures exhibit nanopores when sectioned.

Micropororous Interconnections (also called micropores or microporous passageways): Voids found in lamellar pore walls. Each strut or lamellae of polymer is separated from each other by elongated, parallel pore structures called micropores. The size of these pores is less than 200 $\mu$m. Micropores contribute to the overall interconnectivity of the scaffolds.

Macroporous interconnections: passageways between lamellar arrays of pore walls, or between polymer struts. They contribute mostly to the interconnectivity of the macropores, and range in size between 200 $\mu$m and 2 mm.

Nanopores: Voids found in the bulk of the polymer. Cross-sections of bulk polymer material, either from pore wall struts or pore wall lamellar structures, exhibit rounded concavities that may, or may not, perforate the entire polymer bulk material. These nanopores may result from trapped non-solvent within the bulk of the polymer, or from autocatalytic degradation of the bulk of the polymer. Nanopores are distributed in the walls of the scaffold. They only contribute to the overall interconnectivity of the macropores when they go through the entire bulk material.

Interconnections: the flow passageways connecting the macropores with each other. The interconnections comprise the macroporous interconnections (passageways), the microporous interconnections (passageways), and the nanopores that perforate the entire bulk material defined above.

The present invention provides a macroporous polymer scaffold comprising macropores and interconnections. Macropores have a diameter in the range of 0.5–3.5 mm, and interconnections as seen in trabecular bone. The morphology of the polymer scaffolds (also referred to as foam structures) disclosed herein is based on that of trabecular bone.

Trabecular bone has been shown to be metabolically the most active site in bone (as described by Rodan G A, in *Bone* 13, S3–S6 1992). The specific open pore geometry of trabecular bone favorably affects bone formation and resorption, and is therefore of considerable interest in the context of bone tissue engineering: indeed, the design of an ideal scaffold for bone tissue engineering should also allow fast bone formation and resorption. The morphology of bone trabeculae has therefore served as a model to create the new polymer scaffold structures disclosed herein.

The architecture of the trabeculae of bone depends on the anatomicsite where the bone is found and, to a lesser extent, on the age of the patient.

Figure 2:
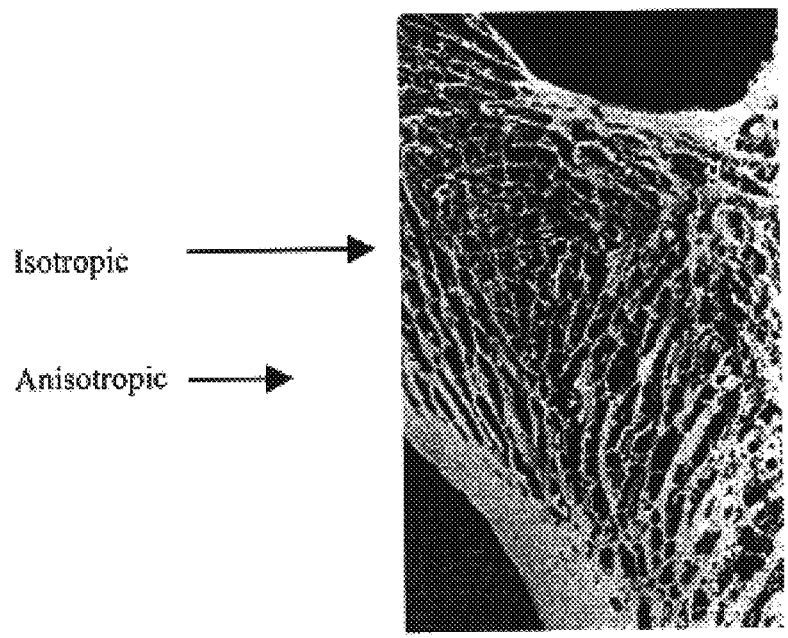
FIG. 2 is a light micrograph of the bone trabeculae in the neck of the femora showing the isotropic and anisotropic areas (Modified light micrograph from Tobin W. J., in *J. Bone Jt Surg* 37A(1) 57–72, 1955)

Martin R B (in *CRC Critical Reviews in Biomedical Engineering,* 10(3), 179–222, 1984) described the trabeculae of bone as "a complex system of interrupted walls and struts". The voids found between the trabeculae are called "marrow spaces". The directions of the trabeculae are irregular; however, a global organization of the trabecular geometry is sometimes visible and follows the forces acting on the bone. Areas where trabeculae follow a given direction are anisotropic whereas areas where trabeculae are disposed randomly are isotropic (cf. FIG. 2).

Whitehouse and Dyson (supra) as well as Martin (supra) described the porosity of the trabeculae bone in the femora in great detail. Table 1.1 indicates different porosities and trabecular width determined by Whitehouse and Dyson for all areas of the femora.

TABLE 1.1

Femoral trabecular bone porosity and trabeculae width.

| Area | Porosity (% void/bone) | Trabeculae width (mm) |
| --- | --- | --- |
| Medial | 71.5 ± 5.0 | 0.23 ± 0.060 |
| Lateral | 79.0 ± 5.0 | 0.23 ± 0.053 |
| Intertrochanteric arches | 88.2 ± 3.2 | 0.14 ± 0.029 |
| Interior of Intertrochantric arches | 84.5 ± 1.8 | 0.18 ± 0.024 |
| Greater Trochanter | 90.5 ± 1.0 | 0.31 ± 0.026 |

The structure of trabecular bone has been investigated for trabecular width, porosity, anisotropy, and general patterns like connectivity and star volume. Light and scanning electron micrographs published on trabecular bone indicate that the marrow spaces delineated by trabeculae (i.e. pores) range from one to several millimeters in size and are interconnected with holes ranging from approx. 0.3 to one millimeter.

When the use of the trabeculae produced of polymer forming the present invention is for physiological applications, the polymer scaffold is preferably prepared from any biocompatible polymer. The term "biocompatible" as it is used herein is meant to encompass polymers which are not toxic to cells and which allow cells to colonize thereon. Examples of suitable polymers include poly (lactide), poly(lactide-co-glycolide) (PLGA) of varying ratios, polystyrene, poly(glycolide), poly(acrylate)s, poly (methyl methacrylate), poly(hydroxyethyl methacrylate), poly(vinyl alcohol), poly(carbonate), poly(ethylene-co-vinyl acetate), poly(anhydride), poly(ethylene), poly (propylene), poly(hydroxybutyrate), poly(hydroxyvalerate), poly(urethane)s, poly(ether urethane), poly(ester urethane), poly(arylate), poly(imide), poly(anhydride-co-imide), poly (aminoacids) and poly(phosphazene). Biodegradable, aliphatic polyesters such as polylactic acid, and polymers derived therefrom, represent a particularly useful class of polymers in applications of the present scaffolds, which relate to cell transplantation due to the fact that they have already been approved for human clinical use. In this regard, a preferred polymer for use as scaffold is PLGA, particularly blends comprising more than 50% poly(DL-lactide) such as PLGA 85:15 and PLGA 75:25.

Suitable applications for the present scaffolds will vary with polymer composition and structure. For example, biodegradable polymer scaffolds are suitable for use in either, in vitro applications and/or in vivo cell transplantation. The matrices may serve then as supports or scaffolds to allow cell growth to occur in vitro prior to implantation in vivo. The scaffolds may also be used directly in vivo, without being pre-seeded with cells. In both applications (with or without prior cell seeding), biodegradable polymer matrices in accordance with the present invention are particularly useful for the growth of three-dimensional tissue and may be used in the growth of connective tissues, like bone, cartilage, paradontal tissue, as well as dental tissues and other organs, such as liver or breast tissue.

A significant characteristic of the present polymer scaffold is the presence of macropores at least 50% of which have a diameter within the range of 0.5 to 3.5 mm, a range representative of that found in the human trabecular bone. Preferably, the macropores have a diameter of at least 1.0 mm, and most preferably, the macropores have a diameter between about 1.0 mm and 3.5 mm.

In addition to its macroporous structure, the scaffold is also characterized by a high level of interconnectivity which enhances both penetration of the scaffold by cells and nutrient flow to cells. Macroporous interconnections of at least 0.35 mm provide an "open cell" environment in the polymer scaffold, which is important to encourage tissue growth throughout the scaffold, i.e. three-dimensional tissue growth.

The macropores are delineated by porous polymer walls that may or may not exhibit a lamellar structure. Total thickness of the pore walls is no greater than about 0.4 mm, and preferably no greater than about 0.3 mm. The degree of interconnectivity in the pore walls is dependent, upon other factors, of the processing temperatures.

A suprising and unexpected result is that each macropore is in flow communication with a significant number of neighboring macropores via both macro- and microporous interconnections.

Scaffolds with different pore wall structures obtained at different processing temperatures using this novel phase inversion particulate leaching process are described in the present document.

The porosity of the polymer scaffold is at least at a level of 50% for all scaffolds obtained, as estimated using Northern Eclipse image analysis software and preferably at a level of greater than 50%. The level of porosity of the present polymer scaffold also contributes to the "open cell" nature thereof, resulting in significant overlap between macropores (giving rise to the macroporous passageways) which defines the highly interconnected nature of the present scaffold and further enhances its utility as a scaffold for cell growth. In this regard, the level of porosity is preferably greater than about 75%, while the most preferred level of porosity is greater than about 85%.

The features of the present scaffold make it particularly suitable for use in tissue engineering and more notably, cell transplantation, because it provides a biocompatible scaffold that cells can colonize in a three-dimensional manner via the interconnected macroporous network of the scaffold. This is significant when considering the transplantation of any cells that yield tissues, especially those requiring neoangiogenesis such as bone tissue. Moreover, when used for cell transplantation, the scaffold is biodegradable, the degradation of which can be controlled such that cell growth may be simultaneous with the degradation of the scaffold.

It will be understood by those of skill in the art that the present polymer scaffold may be modified in order to enhance further its properties for use as a scaffold for cellular growth. Modifications typically effecting the structures used as support for cellular growth would also be suitable to modify the present polymer scaffold. Such modifications function to enhance biological response and include, for example, surface modifications with collagen, calcium phosphate, proteoglycans, proteins, peptides, carbohydrates and polysaccharides, or by acid/base treatment. Additionally, the polymer scaffold may serve as a reservoir for the delivery of active molecules, such as proteins, growth factors, etc. that enhance cellular function.

The present polymer scaffold can be made using a novel process which combines particulate leaching methodology with phase inversion methodology. In an initial step, the selected polymer scaffold is prepared as a liquid polymer. As used herein, the term a liquid polymer is meant to refer to polymer in liquid form, either alone or admixed with another liquid. This may be done by mixing the polymer in a solvent to form a polymer solution. Any solvent generally useful to prepare a polymer solution can be used for this purpose, including dimethylsulfoxide (DMSO), methylene chloride, ethyl acetate, chloroform, acetone, benzene, 2-butanone, carbon tetrachloride, chloroform, n-heptane, n-hexane and n-pentane. As one of skill in the art will appreciate, non-cytotoxic solvents such as DMSO are preferably used to prepare the solution so as not to adversely affect cellular growth. The concentration of the polymer in the polymer solution will vary with the characteristics of the polymer used to make the scaffold. Alternatively, the polymer can be formed into a liquid polymer by heating to its melting point.

The liquid polymer Is then admixed with particles of an appropriate size in connection with the particulate leaching phase of the process. Particles having a diameter corresponding to the desired diameter of the macropores in the polymer scaffold are suitable, specifically particles having a diameter in the range of 0.5–3.5 mm. More preferably, the particles have a diameter of greater than 1.0 mm and most preferably, the particles have a diameter of between 1.0 and 2.0 mm. Examples of suitable particles for admixture with the polymer include polysaccharides (such as glucose), organic and inorganic salts, proteins and lipids of an appropriate size which can be dissolved in a solvent other than a solvent for the polymer (i.e. a polymer non-solvent). The amount of particles admixed with the polymer solution will again vary with the characteristics of the polymer used to make the present scaffold.

Once the particles have been thoroughly mixed with the liquid polymer to form a particulate polymer mixture, the polymer is subjected to a phase inversion step in which it is converted from a liquid to a solid. This step is achieved by submerging the particulate polymer mixture in a polymer non-solvent, a solvent in which the polymer is not soluble. Such polymer non-solvent include, for example, water, alcohol, 1–4 dioxane and aniline.

In order to obtain a solid polymer scaffold in a particular shape, the polymer mixture can be placed in a mold during the phase inversion step. Preferably, the liquid polymer can be stabilized around the particulates by, for example, freezing the polymer-particulate slurry. Thereby, no mold is used and the phase inversion process occurs simultaneously from all outer surfaces. When the polymer solvent is DMSO, for example, the polymer mixture is cooled to a temperature less than or equal to 12° C., which is the freezing temperature of DMSO. Cooler temperatures, such as temperatures of less than 0° C. can also be used. A consequence of using low temperatures (for example, −20° C. or −80° C.) during this stage of the process is the subsequent formation of a polymer scaffold with a different morphology (cf Example 4), like a thicker skin structure, which may be removed prior to use as a scaffold for three-dimensional cell growth, as described in Example 1. In addition to cooling, other methods of stabilizing the polymer-particulate mixture may be used, for example gellation (increasing viscosity).

Following conversion of the polymer mixture from liquid to solid phase, the polymer is subjected to particulate leaching. In this step of the process, the polymer is immersed in a particulate solvent, i.e. a solvent which functions to dissolve the particles dispersed throughout the polymer but does not dissolve the polymer itself. Appropriate particulate solvents will, of course, depend on the nature of the particles and the polymer. Examples of appropriate particulate solvents include water, alcohol, 1–4 dioxane and aniline. The temperature of the particulate solvent can be varied with minimal effect on the resulting polymer scaffold. However, the temperature will generally be between the freezing point of the particulate solvent and the glass transition temperature of the polymer, so that the polymer scaffold does not melt or become viscous under the effect of the non-solvent temperature. In one example, a particulate solvent temperature of between about 0° C. and 45° C. is applied when the particulate solvent is water and the polymer is PLGA 75:25.

The polymer is submerged in the particulate solvent for an amount of time appropriate to allow complete dissolution of the particles dispersed throughout the polymer scaffold. Generally, a period of at least 24 hours is required to obtain complete particulate dissolution in the polymer scaffold, while a period of at least 48 hours is preferred. In order to expedite efficient dissolution of the particles, it is desirable to immerse the polymer in fresh solvent at frequent intervals during the dissolution period, for example at approximately 8–9 hour intervals or by the use of a circulating solvent bath.

The phase-inversion and particulate-leaching processes may occur in one step with a solvent that is simultaneously a polymer non-solvent and a particulate solvent. In one example, double distilled water ($ddH_2O$) was used The polymer scaffold is removed from the particulate solvent following an appropriate particulate dissolution period and can be either vacuum-dried prior to use or disinfected in alcohol (such as 70% ethanol), rinsed and conditioned in culture medium for subsequent use. If the polymer scaffold is not required for immediate use, it is desirably stored dry in a dessicator to prevent moisture retention and possible degradation of the polymer.

The present process advantageously yields a polymer scaffold having unique characteristics, and in particular, yields a polymer scaffold having an interconnected macroporous network. Another significant advantage of the present two-stage process is that it provides amplified means for controlling the morphology of the resulting polymer scaffold. In other words, the process provides two levels, particulate leaching and phase inversion, at which to effect the morphology of the polymer scaffold. For example, macropore size and distribution can be altered during both, the particulate leaching and phase inversion stage of the process and are governed by particulate size and distribution, and, to a lesser extend by the scaffold processing temperatures. In addition, interconnection formation and size can be influenced by varying the rate of the phase inversion. The rate of the phase inversion can be altered altering a number of variables including temperature, type of polymer non-solvent and polymer concentration. Thus the final scaffold morphology can be controlled. Preferably, the resultant morphology resembles that of human trabecular bone.

In another aspect of the present invention, a method for culturing cells for three-dimensional growth is provided utilizing the polymer scaffold described herein. The novel interconnected macroporous structure of the present polymer scaffold is especially suitable for tissue engineering, and notably bone tissue engineering, an intriguing alternative to currently available bone repair therapies. In this regard, bone marrow-derived cell seeding of the polymer scaffold is performed using conventional methods, which are well known to those of skill in the art (as described in Maniatopoulos et al, in *Cell Tissue Res* 254, 317–330, 1988). Cells are seeded onto the polymer scaffold and cultured under suitable growth conditions. The cultures are fed with media appropriate to establish the growth thereof.

As set out above, cells of various types can be grown throughout the present polymer scaffold. However, the polymer scaffold of the present invention is particularly suited for the growth of osteogenic cells, especially cells that elaborate bone matrix. For tissue engineering, the cells may be of any origin. The cells are advantageously of human origin. The present method of growing cells in a three dimensional polymer scaffold according to the invention allows seeded osteogenic cells, for example, to penetrate the polymer scaffold to elaborate bone matrix, during the in vitro stage, with pervasive distribution in the structure of the polymer scaffold and particularly to a depth of at least 2.5 times the depth of the average macropore size. Osteogenic cell penetration and, as a result, bone matrix elaboration can be enhanced by mechanical, ultrasonic, electric field or electronic means.

Embodiments of the present invention are described in the following specific examples which are exemplary only and not to be construed as limiting.

EXAMPLE 1

Preparation of a PLGA 75:25 Polymer Scaffold

A PLGA 75:25 polymer scaffold in accordance with the present invention was prepared using PLGA 75:25 (obtained from Birmingham Polymer Inc), having an inherent viscosity of 0.87 dL/g. One ml of 0.1 g/ml of PLGA 75:25 in DMSO was mixed with 2 g of glucose crystals (particle size ranging from 0.8 mm to 2 mm) in an aluminum mold. The PLGA 75:25-DMSO mixture was cooled to −20° C. This temperature of the PLGA 75:25-DMSO mixture is referred to $T_{mix}$. The frozen PLGA 75:25 blocks were then immersed in an ice-water slurry of ddH$_2$O at 0° C., which is a non-solvent for the polymer. This temperature of the water is referred to $T_{nonsolvent}$. The blocks remained in ddH$_2$O for 48 hours during which the ddH$_2$O was changed approximately every 8 hours. The obtained scaffolds were then removed from the water, vacuum-dried for 72 h at 0.01 mm Hg and stored at 4° C. in a desiccator under vacuum until use. Scaffolds obtained using the above mentioned conditions were then fully analyzed.

Figure 3A:
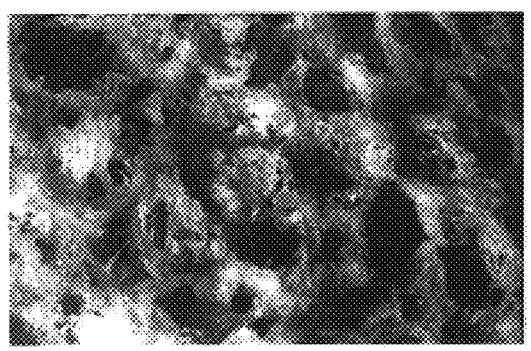
FIG. 3A is a light micrograph of a polymer in accordance with the present invention (field width=1.8 cm)

The macroporous structure of 2 mm thick polymer scaffold sections was observed at low magnification (16×) using a dissection microscope as shown in FIG. 3A. A uniform distribution of interconnected macropores ranging in size from about 0.8–1.5 mm was observed throughout the polymer scaffold. The macropores exhibited elliptic morphologies and thick porous walls (about 300 μm thick) containing micropores.

Figure 3B:
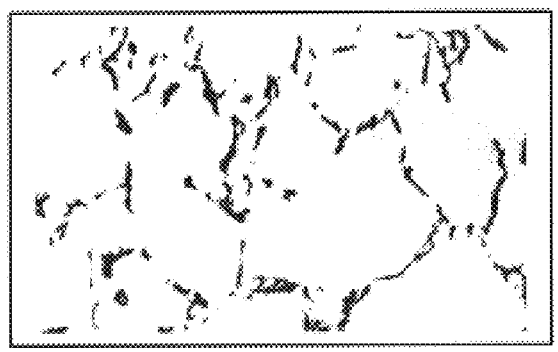
FIG. 3B is a light micrograph of a 20μm section of the polymer scaffold of FIG. 3A (field width=3.5 mm)

The polymer scaffold was then embedded in Tissue-Tek embedding medium (Miles #4583), and sectioned in a cryostat at −20° C. A serial set of 20 μm-thick sections (50 sections) were collected on glass slides (VWR Canlab). Sections were photographed at low magnification (16×) using a dissecting microscope and scanned. FIG. 3B is a scanned scaffold section that identifies the porous components of the scaffold, the macropores, the macroporous interconnections (passageways) and the microporous interconnections (passageways). A polymer thin film (i.e. a skin layer) was observed on the outer surface of the polymer scaffold. The images were converted to TIFF files and analyzed on a PC computer using the Northern Eclipse image analysis software. The "single measurement" menu was used to measure the pore wall sizes (area, perimeter, diameter etc.) for each scanned section. The "data measure" routine computed the area and number of pore wall struts per scanned slide.

These measurements were converted from pixel units to millimeters by calibrating the system, using the above mentioned magnification of the scanned images to determine the pixel/mm ratio. Macropore size was determined by manually drawing a line with a software tool on the digitized image of the polymer scaffold section from one pore wall to the adjacent pore wall. The characteristics of the resulting polymer scaffold as determined using the Northern Eclipse image analysis software were as follows:

| | |
|---|---|
| Macropore Size | 1.79 +/− 0.42 mm |
| Macroporous interconnections | 0.37 +/− 0.15 mm |
| Pore wall thickness | 0.29 +/− 0.13 mm |
| Micropores | 0.10 +/− 0.05 mm |
| Porosity | 86.7 +/− 2.43% |

The porosity of the polymer matrices was also estimated by mercury porosimetry (Quantachrome Autoscan 60). A solid penetrometer with 5 cm$^3$ cell stem volume was used for samples in the range of 0.015 to 0.020 g. The values of void volume were calculated from the mercury intrusion volume. The porosity was calculated from the mercury intrusion volume to be 89.6%. The porosity estimated using the Northern Eclipse image analysis software (~87%) is substantially equivalent to that of ~90% as measured by mercury porosimetry given that the mercury porosimetry method is not accurate when analyzing polymer scaffolds with pore diameters greater than ~75 μm.

The polymer scaffold was also prepared for analysis using a scanning electron microscope (SEM). The scaffold was cross-sectioned at a thickness of approximately 2 mm and sputter-coated with gold under argon atmosphere (Polaron Instrument Inc., Doylestown, Pa.). Scanning electron micrographs were taken on a Hitachi 2500 SEM at 15 kV acceleration voltage. The diameter of the macropores was confirmed using the SEM micrographs to be about 1 to 1.5 mm, although a clear separation between each macropore was not always observed illustrating the very open interconnected structure of these polymer scaffolds.

Figure 3C:
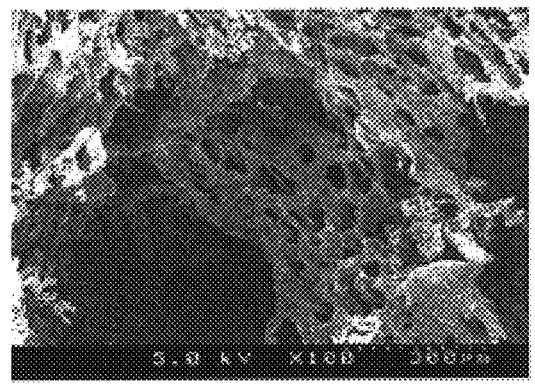
FIG. 3C is a scanning electron micrograph of the pore walls of the polymer scaffold of FIG. 3A.

The microporous nature of the pore walls, as observed under the optical microscope, was confirmed by SEM, as shown in FIG. 3C.

Figure 4A:
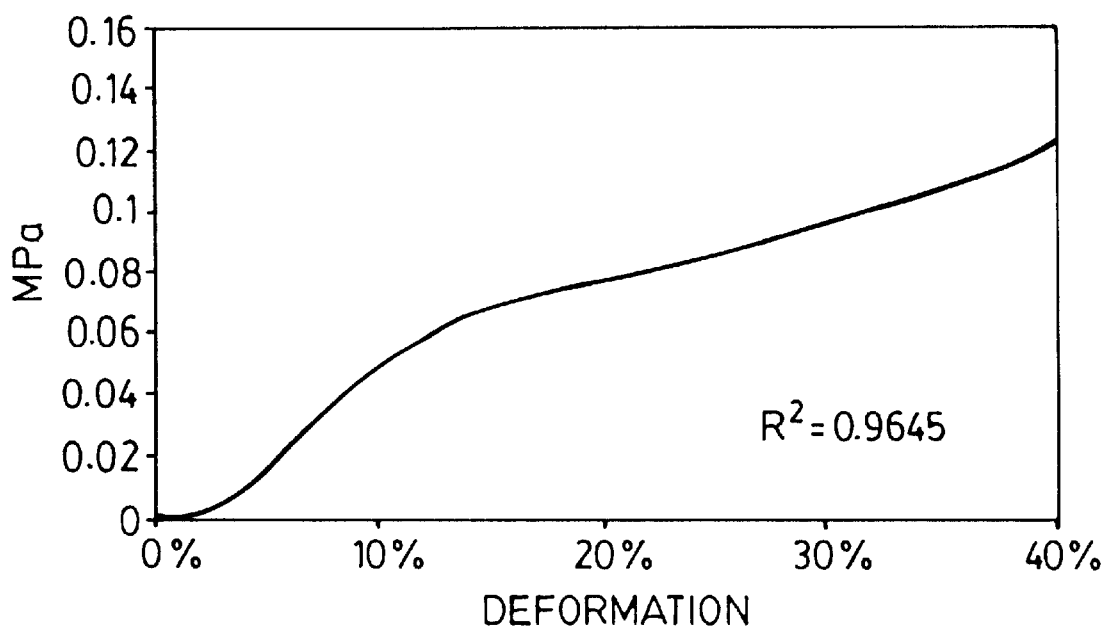
FIG. 4A is a chart illustrating the stress/strength curve of the polymer scaffolds when submitted to a compressive test at a rate of 1% deformation per second.

The polymer scaffold was mechanically tested as follows. A polymer scaffold in the form of a cylinder with a diameter and a height of 1.5 cm was prepared and tested using an Instron Mechanical tester. The mechanical experiments were performed on a uniaxial servohydraulic testing machine (Instron Model 1331 load frame with Series 2150 controller). A 1 kg load cell (Sensotec, Model 31/4680) was used for all compression tests. The deflection of the actuator was measured by a DC linearly variable differential transformer (LVDT, intertechnology Model SE 374). Signals from the load cell and the LVDT were displayed during testing on a digital storage oscilloscope (Gould, Model 1425). The signals were also input into a 16-channel, 12-bit analog-to-digital (A/D) converter in an accelerated Apple IIe computer. The rate of data acquisition for these experiments was 430 pairs of data points per second. Compression of the polymer scaffold occurred at a rate of 0.1 mm/s. As shown in FIG. 4A, A plot of compression strength vs. percent deformation of the polymer scaffold showed two moduli. The Young's modulus for the first elastic region (referred to $Y_1$) was 0.76±0.12 MPa, and for the second elastic region (referred to $Y_2$) was 0.18±0.016 MPa.

EXAMPLE 2

Effect of Polymer Concentration on Polymer Scaffold Structure

The effect of PLGA 75:25 concentration in DMSO on the structure of the resulting polymer scaffold was determined using the protocol outlined in detail in Example 1. Three different concentrations of PLGA 75:25 in DMSO (0.05 g/ml, 0.1 g/ml and 0.2 g/ml) were used to make polymer matrices while all other conditions were maintained constant as described in Example 1.

Figure 4B:
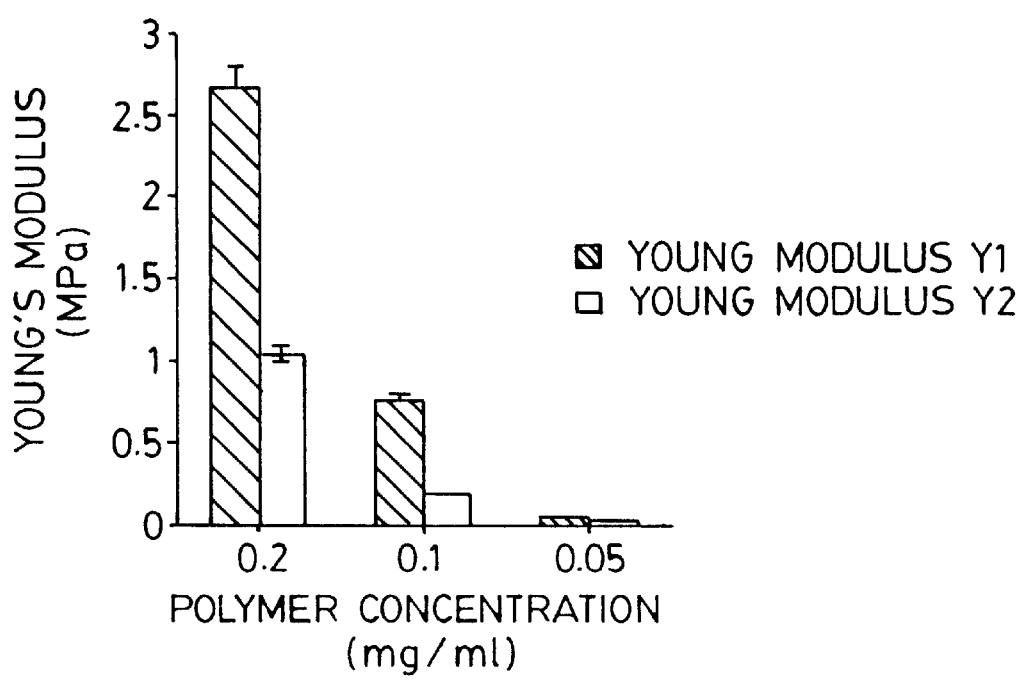
FIG. 4B is a chart illustrating the effect of polymer concentration on mechanical properties of polymer scaffolds. The Young Modulus of the first elastic region is referred to $Y_1$ and the Young Modulus of the second elastic region is referred to $Y_2$.

Each of the polymer scaffolds prepared were cut in half using a razor blade. A skin structure was found on each regardless of the starting concentration of PLGA 75:25 in DMSO. The mechanical properties of the 3 different polymer scaffolds were assessed and are illustrated in FIG. 4B. A significant decrease in Young's modulus was observed in the polymer scaffold prepared using the PLGA in DMSO of 0.05 mg/ml while the stiffest scaffold was obtained with a PLGA 75:25 concentration of 2 mg/ml.

Figure 5:
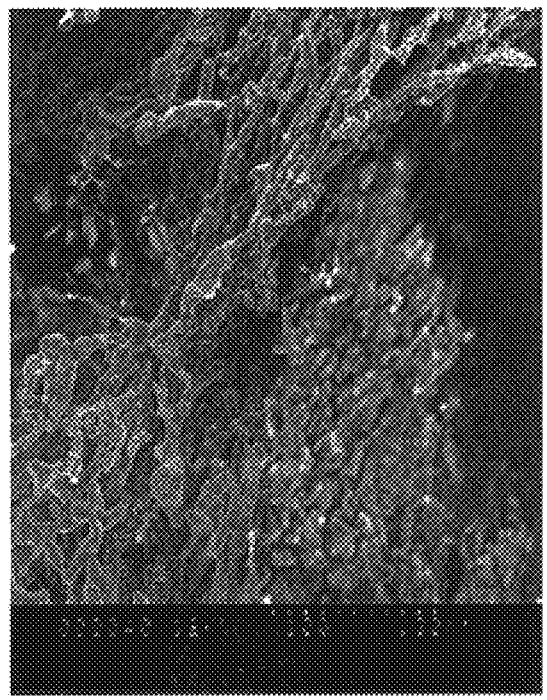
FIG. 5 is a scanning electron micrograph of the pore wall structure of a scaffold prepared with a concentration of 0.05 g/ml PLGA 75:25 in DMSO.
Figure 6:
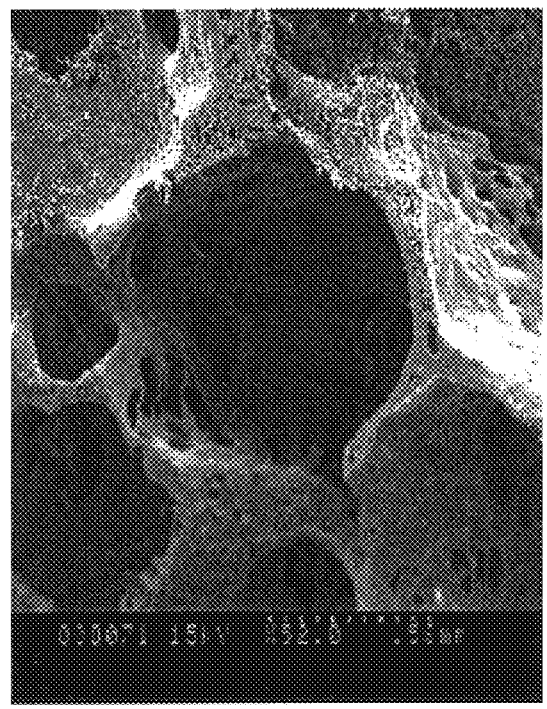
FIG. 6 is a scanning electron micrograph of the pore wall structure of a scaffold prepared with a concentration of 0.2 g/ml PLGA 75:25 in DMSO.

These scaffolds were also observed under light microscopy and SEM. No differences in structure could be detected between the three polymer scaffolds under light microscope. However, when observed under the SEM, the scaffolds created with 0.05 g/ml PLGA in DMSO exhibited more of a lamellar wall structure with more microporous interconnections (see FIG. 5), than those created with 0.2 g/ml PLGA in DMSO, where fewer microporous porous interconnections were seen (see FIG. 6).

EXAMPLE 3

Effect of the Particles on Polymer Scaffold Structure

The effect on polymer scaffold structure of both varying the amount and size of the glucose particles admixed with the PLGA polymer was determined as follows. Differing amounts of glucose particles (0.5 g, 1 g and 2 g) were separately admixed with 1 ml polymer solution, maintaining all other conditions as described in Example 1 constant. The effect of particle size on the final scaffold morphology was also assessed by using the following sieved particles: (standard testing sieves, VWR, West Chester, Pa.): 1) NaCl crystals (<0.35 mm), 2) sucrose crystals (0.54 mm<crystal size<0.8 mm) and 3) glucose crystals (0.8 mm<crystal size<2 mm). The resulting polymer scaffolds were observed by light microscopy. When mixing the polymer solution with the particulates, it was seen that for small amounts of particulates (i.e. 0.5 g/ml), the polymer solution was not fully immersed in the particulate bed. This layer of polymer solution resulted after phase inversion in a membranous structure, similar to that seen when no particulates are used. Larger solution densities of particulates (i.e. 2.0 g/ml) completely infiltrated the polymer solution so that the resulting scaffold contained a distribution of macropores without this membranous structure.

Figure 7A:
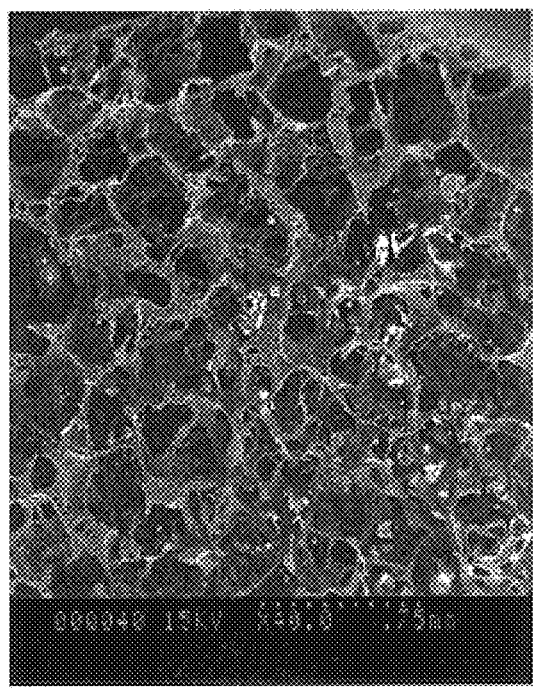
FIG. 7A is a scanning electron micrograph of PLGA 75/25 scaffolds obtained using particles less than 0.35 mm.
Figure 7B:
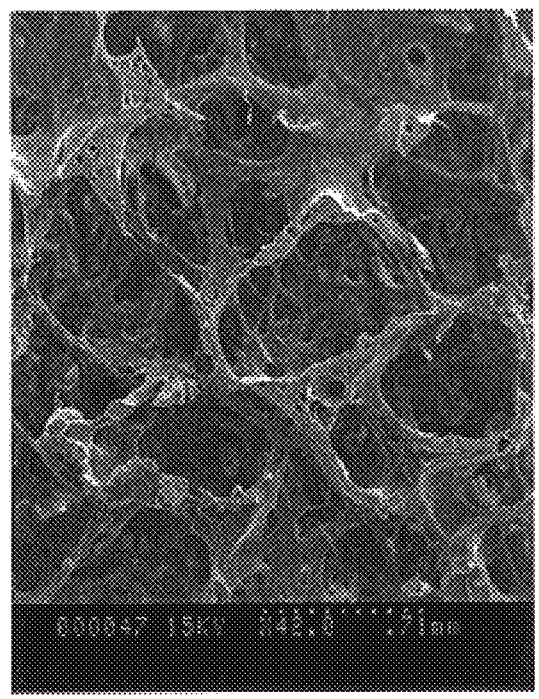
FIG. 7B is a scanning electron micrograph of PLGA 75/25 scaffolds obtained using particles ranging from 0.54 t 0.8 mm.
Figure 7C:
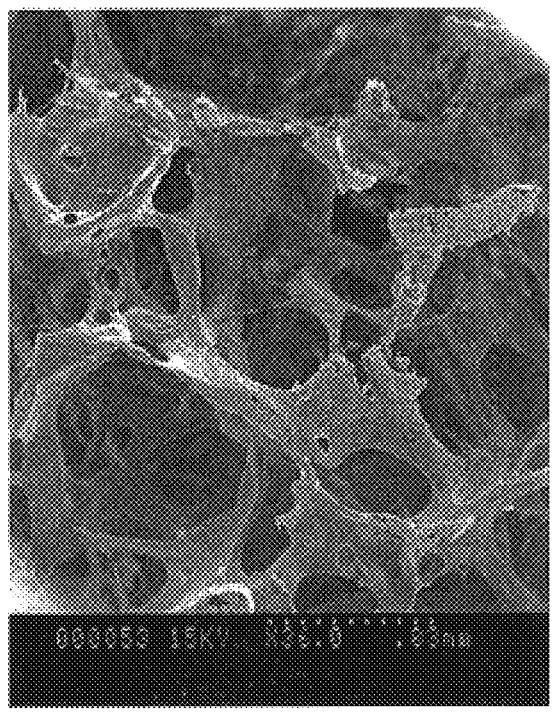
FIG. 7C is a scanning electron micrograph of PLGA 75/25 scaffolds obtained using particles ranging from 0.8 to 2.0 mm.
Figure 8:
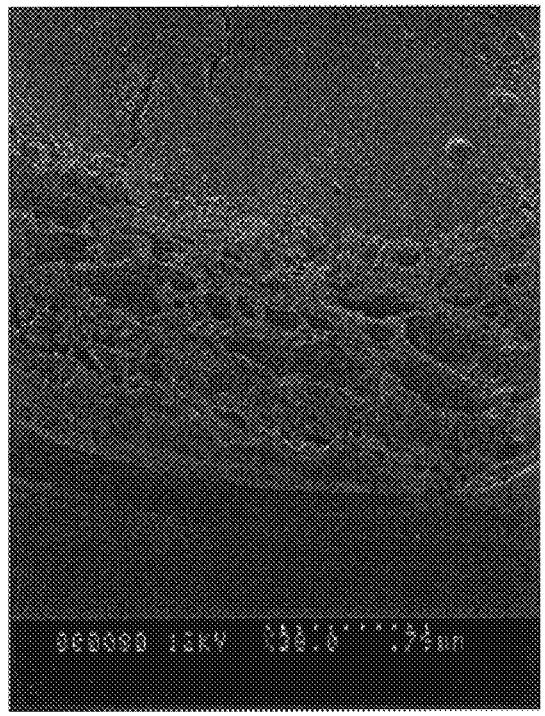
FIG. 8 is a scanning electron micrograph of a PLGA 75/25 membrane prepared in absence of particles.

The size of the macropores was directly proportional to the size of the particles used, e.g. macropore size were ~0.33 mm when particles <0.35 mm were used (cf. FIG. 7A), and ~0.75 mm when particles ranging from 0.54 to 0.8 mm were used (cf. FIG. 7B). Finally for particles bigger than 0.8 mm, the observed macropores were ~1.4 mm (cf FIG. 7C). When no particles were mixed to the polymer-DMSO solution, the resulting polymer structure was a hollow cylinder composed of a thick skin containing micropores, as illustrated in FIG. 8. This skin closely resembled the membrane structure resulting from a normal phase-inversion process.

EXAMPLE 4

Effect of the Processing Temperatures on Polymer Scaffold Structure

Figure 9A:
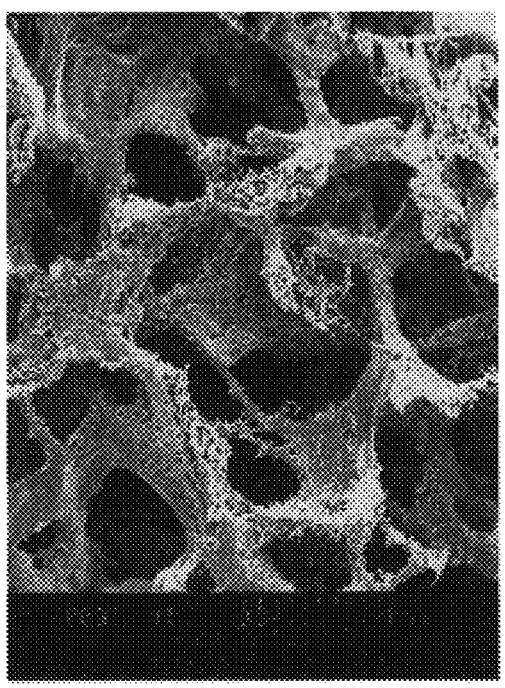
FIG. 9A is a scanning electron micrograph of a PLGA 75/25 foam obtained at Tmix=11° C., and Tnonsolvent=0° C.

The effects of three different $T_{mix}$ (11° C., -20° C. and -80° C.) at constant $T_{nonsolvent}$ (0° C.) were studied. Two main different scaffold structures were obtained: 1) with $T_{mix}$=11° C. and 2) with $T_{mix}$=-20° C. and $T_{mix}$=-80° C. Scaffolds obtained with a $T_{mix}$=11° C. and a $T_{nonsolvent}$=0° C. were skinless and showed a very open structure. As shown in FIG. 9A, The macropores sizes seemed expanded, and were estimated by SEM at to ~2.72 mm. The pore walls had less micropores but more macroporous interconnections, providing a generally more open structure to the scaffolds. The scaffolds obtained for $T_{mix}$=-20° C. and -80° C. both had a skin structure. For $T_{mix}$=-20° C. the macropores seemed smaller than on scaffolds obtained at higher $T_{mix}$ and their sizes were estimated by SEM at ~1.8 mm. The pore walls were lamellar, with fewer macroporous interconnections but more microporous interconnections (of FIG. 9B). It was observed that the macropore size decreased with lower $T_{mix}$. The differences in macropore sizes were particularly important between scaffolds created at $T_{mix}$=11° C. and $T_{mix}$=-20° C., whereas minor differences in macropore size were observed between scaffolds created at $T_{mix}$=-20° C. and $T_{mix}$=-80° C. While the macropore sizes diminished with $T_{mix}$ the structure of the pore wall also changed as described above. Differences in $T_{mix}$ may have affected the rate of polymer precipitation, and therefore, the complexity of the pore wall structure.

Figure 9B:
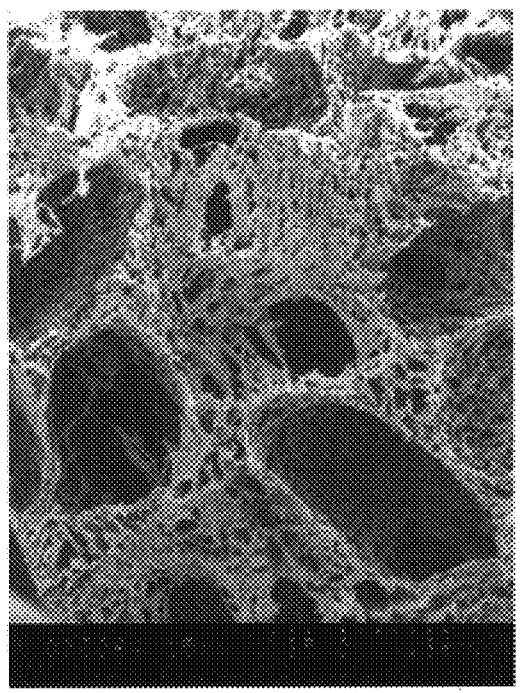
FIG. 9B is a scanning electron micrograph of a PLGA 75/25 foam obtained at Tmix=−20° C., and Tnonsolvent=0° C.
Figure 9C:
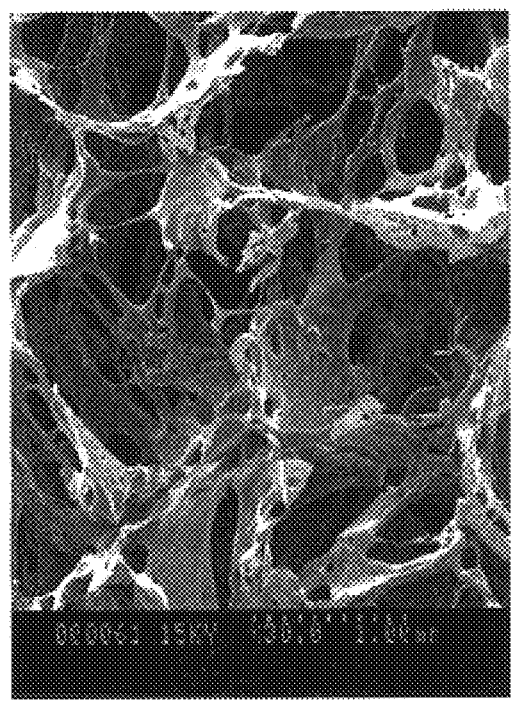
FIG. 9C is a scanning electron micrograph of a PLGA 75/25 foam obtained at Tmix=−20° C., and Tnonsolvent=40° C.

Different $T_{nonsolvent}$ (40° C., 20° C. and 0° C.) were also studied, with a constant $T_{mix}$ of -20° C. In this case, the main difference between all scaffolds was their pore wall thickness. Lower $T_{nonsolvent}$ caused thicker and more complex pore walls whereas higher $T_{nonsolvent}$ created thin and compact pore walls, comparable to polymer struts delineating each macropore. FIGS. 9B and 9C show the different morphologies of the scaffold structures at $T_{nonsolvent}$=0° C. and 40° C. respectively. Most structural differences were seen between scaffolds created at $T_{nonsolvent}$=0° C. and $T_{nonsolvent}$=20° C. Fewer differences were seen between scaffolds obtained at $T_{nonsolvent}$=20° C. or 40° C. While lower $T_{nonsolvent}$ (0° C.) provided lamellar pore walls (cf FIG. 9B), higher $T_{nonsolvent}$ (40° C.) provided strut-like pore wall morphologies (cf FIG. 9C).

The thickness of the pore walls of scaffolds created at different $T_{nonsolvent}$ was estimated by SEM. At $T_{nonsolvent}$=0° C., the pore walls were estimated at 0.29 mm, whereas at $T_{nonsolvent}$=20° C., the size of the pore walls was ~0.10 mm; and no significant differences could be measured between $T_{nonsolvent}$=20° C. and 40° C. All scaffolds created with the various temperatures as mentioned above were sectioned, and pore size and pore wall thickness were measured. Their porosity was also estimated using the Northern Eclipse image analysis software. The following results were obtained:

| Temperature of Polymer solution (° C.) | Temperature of non-solvent (° C.) | Pore size ± std dev. (mm) | Pore wall thickness ± std dev. (mm) | Porosity (%) |
| --- | --- | --- | --- | --- |
| −80 | 0 | 1.71 ± 0.22 | 0.28 ± 0.16 | 80.4 ± 1.34 |
|  | RT | 1.63 ± 0.32 | 0.24 ± 0.10 | 83.8 ± 1.79 |
|  | 40 | 1.91 ± 0.43 | 0.16 ± 0.05 | 84.6 ± 3.65 |
| −20 | 0 | 1.76 ± 0.42 | 0.29 ± 0.13 | 86.7 ± 2.43 |
|  | RT | 2.21 ± 0.43 | 0.10 ± 0.05 | 85.7 ± 0.97 |
|  | 40 | 1.96 ± 0.41 | 0.12 ± 0.04 | 93.1 ± 2.45 |
| 11 | 0 | 2.02 ± 0.54 | 0.11 ± 0.05 | 93.4 ± 2.07 |
|  | RT | 2.41 ± 0.54 | 0.15 ± 0.06 | 91.7 ± 1.63 |
|  | 40 | 2.72 ± 0.41 | 0.17 ± 0.08 | 95.6 ± 1.7 |

EXAMPLE 5

Surface Modification of Polymer Scaffold

The obtained scaffolds as described in Example 1 were further surface modified by acid/base treatment; collagen deposition; and calcium phosphate deposition. The procedures and results were as follows:

Acid/base treatment was developed to enhance surface charge and to change the surface topography. The scaffolds were maintained in several concentrations of acetic acid (0.1M, 1M, 5M) for 24 h. Scaffolds were also maintained in various concentrations of NaOH for 24 h to observe surface polymer chain hydrolysis. Under SEM, the scaffolds treated with 5M acetic acid or 0.1 M NaOH for 24 hours showed changes in surface topography with appearance of nanopores.

A collagen deposition experiment was designed to enhance cell adhesion on the polymer surfaces. The scaffolds were maintained in 0.1% collagen for 1 h, 5 h, 8 h and 24 h.

A calcium phosphate deposition experiment was tested to enhance cell adhesion on the surface of the scaffolds. These were maintained for 1 week in fully supplemented medium (as described in Example 6) at 37° C. The calcium phosphate crystals on the surface of the scaffolds were visualized by Von Kossa staining.

Figure 10:
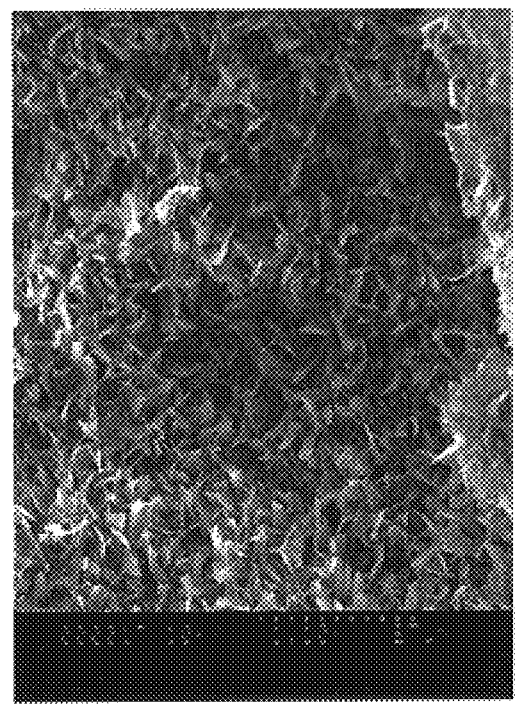
FIG. 10 is a scanning electron micrograph of leaflet CaP coating a PLGA 75/25 scaffold.

Further CaP deposition experiments were conducted, in which the scaffolds were dipped in 1.5 mM $Na_2HPO_4$ for 2 h at room temperature, and further equilibrated in a saturated $Ca^{2+}$ solution overnight. The scaffolds were then observed under SEM and crystals with leaflet morphologies were observed on the scaffold structure. (cf FIG. 10).

EXAMPLE 6

Bone Marrow-Derived Cell Culture on Polymer Scaffolds

PLGA 75:25 polymer scaffolds were prepared as previously described: 2 g/ml glucose crystals were dispersed in a 0.1 g/ml PLGA 75:25 solution in dimethylsulfoxide (DMSO, BDH, Toronto, ON). The polymer slurry was frozen at 11° C. The polymer was then precipitated and the glucose crystals were extracted from the precipitated polymer in $ddH_2O$ at 40° C. Scaffolds were dried to constant mass (10 μm Hg, 72 h), disinfected in 70% EtOH for ½ h, rinsed 3× with α-MEM and equilibrated in sterile α-MEM at 37° C. for 6 days.

First passage primary bone marrow-derived cells were seeded on 0.25 $cm^3$ scaffolds using protocols and media described in detail elsewhere (as described by Maniatopoulos et al, supra, and Davies et al., in Cells and Materials, Jan. 3–15, 1991. Briefly, bone marrow-derived cells were collected from both femora of young adult male Wistar rats (approximately 150 g) into a fully supplemented medium (FSM): α-MEM supplemented with 15% fetal bovine serum, 50 mg/mL ascorbic acid, 10 mM β-glycerophosphate and antibiotics (0.1 mg/mL penicillin G, 0.05 mg/mL gentamicin and 0.3 mg/mL fungizone); $10^{-8}$ M Dexamethasone (Dex) was added to the FSM of only Dex+ cultures.

Cells were maintained in culture for 6 days, and re-fed at days 2 and 5 with FSM. At day 6, Dex− cells were trypsinized with 0.01% trypsin in PBS, whereas Dex+ cultures, in which signs of calcification were visible, were trypsinized with 0.01% trypsin and 10 μM ethylene diamine tetraacetic acid (EDTA) in PBS. Dex+ and Dex− cells were then seeded on separate pre-wetted scaffolds at a concentration of $7.5 \times 10^5$ cells/scaffold. The cultures were maintained for 42 days at 37° C. and 5% $CO_2$ and refed every 2–3 days with FSM. Dex was added to the FSM of Dex+ cell cultures at a concentration of $10^{-8}$M for each refeeding.

Tetracycline•HCl powder (Sigma, St. Louis, Mo.) was dissolved in α-MEM to prepare a stock solution of 90 mg/mL. A new tetracycline-containing fully supplemented medium (TFSM) was prepared of α-MEM containing 15% fetal bovine serum, 50 mg/mL ascorbic acid, 10 mM α-glycerophosphate and 9 mg/ml of tetracycline. The TFSM was used for the last refeeding on day 40. At day 42, cultures were washed in α-MEM (10 times, ~3 min each), and fixed in Karnovsky's fixative (2.0% paraformaldehyde, 2.5% glutaraldehyde and 0.1 M sodium cacodylate buffer, pH 7.2–7.4) overnight A few cultures were kept for SEM observations and were dehydrated in a series of graded alcohol solutions (70%, 100%), and freeze-dried at 0.01 mm Hg for 2 days. All other cultures were kept in 0.1 M Cacodylate buffer for histological or confocal observations.

Figure 11:
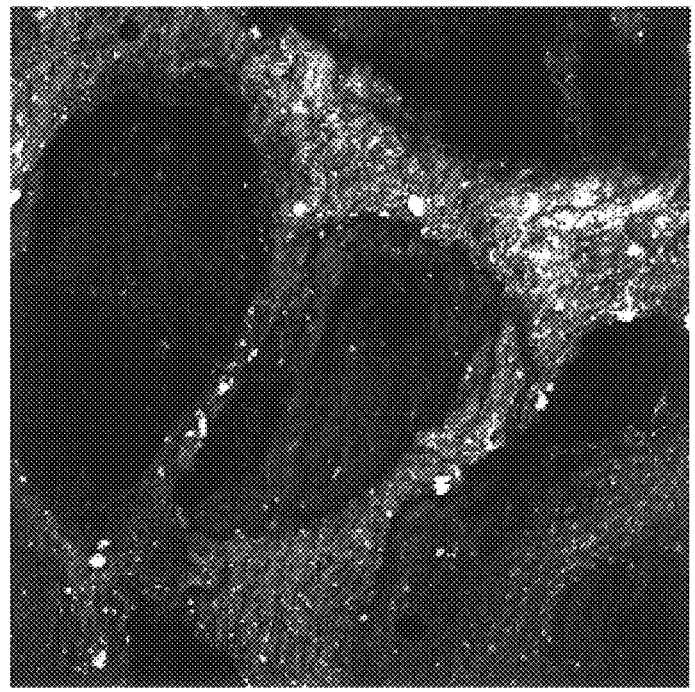
FIG. 11 Is a confocal micrograph of a Dex+ scaffold cultured for 42 days (field width=1.8 mm)
Figure 12:
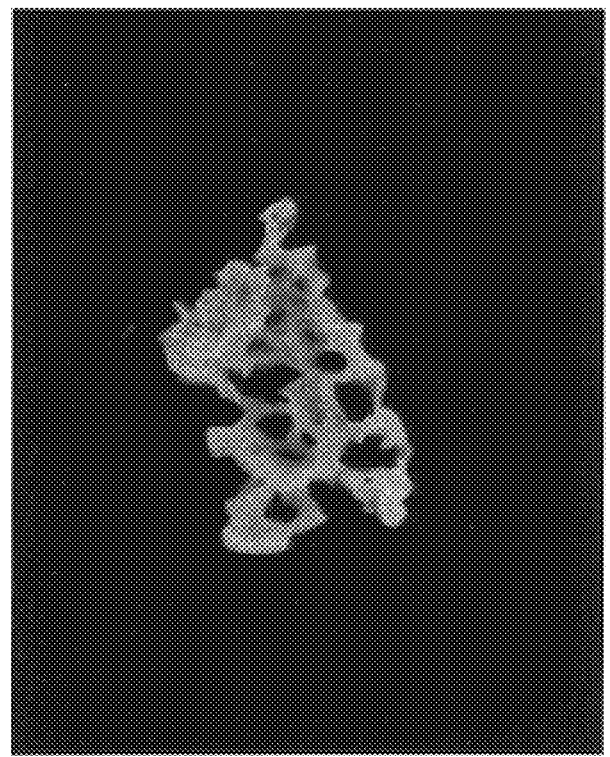
FIG. 12 is a UV-light illuminated light micrograph of a Dex+ scaffold stained with tetracycline. (Field width=2.0 cm)

Confocal observations were carried out as follows: samples were placed in custom-made chambers in 0.1M cacodylate buffer (obtained from BDH). The chambers were sealed with a glass coverslip. Fluorescent signals were detected by optical sectioning in a Bio-Rad MRC-600 confocal laser microscope, using the BHS filter. Scaffold seeded with Dex(+) cells showed a fluorescent label up to a depth of approx. 1 mm as seen in FIG. 11. Fluorescence could not be observed deeper within the scaffolds because the depth of field of the confocal microscope was not sufficient. Scaffolds were therefore sectioned at a thickness of approximately 2 mm and analyzed by confocal microscopy from both sides. Fluorescence was observed throughout the entire scaffold. The fluorescent label was also seen using sections of cell-seeded scaffolds seeded with Dex(+) cells (see FIG. 12). Cross sections of polymer scaffold seeded with Dex(−) and Dex(+) cells were observed under UV light. A bright fluorescent signal was only seen on the Dex(+) sections throughout the whole scaffold. Specifically, the elaborated bone matrix, as observed by the fluorescent signal, was visualized throughout the depth of a 0.5 cm polymer scaffold which was employed in culture. The limiting factor in this assay was the depth of the polymer scaffold; and thus increasing the depth of the polymer scaffold would increase the depth to which cells penetration, and thus bone matrix formation, could be achieved in this polymer scaffold.

Figure 13:
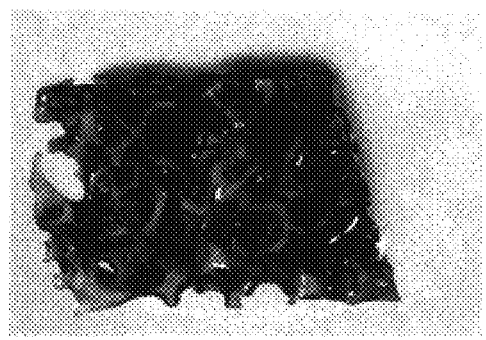
FIG. 13 is a light micrograph of an osteocalcin immunolabeled scaffold. (Field width=1.1 cm)
Figure 14:
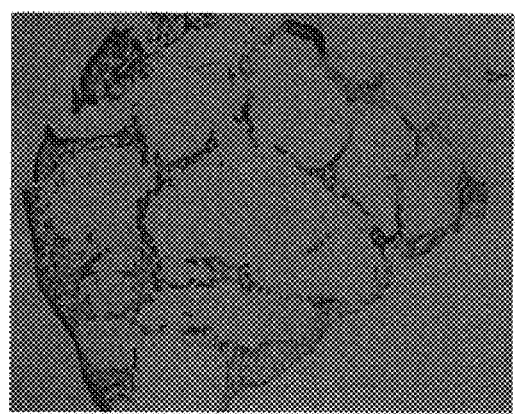
FIG. 14 is a light micrograph of a haematoxylin and eosin stained Dex+ cultured scaffold section. (Field width=0.8 cm)
Figure 15:
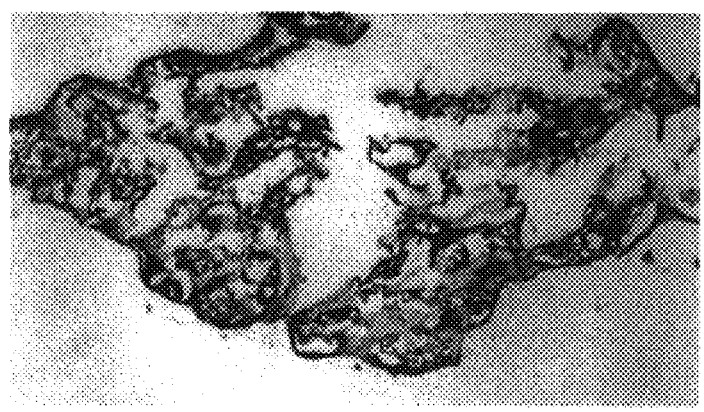
FIG. 15 is a light micrograph of a haematoxylin and eosin stained Dex− cultured scaffold section. (Field width=0.6 cm)

Scaffolds were also immunolabeled for osteocalcin. Osteodalcin expression in both Dex+ and Dex− cultures were assessed by immunohistochemical methods using a goat anti-rat osteocalcin antiserum (Biomedical Technologies Inc., Stoughton Mass.) at a final dilution of 1:6000. The assay was terminated by second anti-body labeling with donkey anti-goat IgG conjugated to horseradish peroxidase antiserum, at a concentration of 1:250. A 3,3-diaminobenzidine (DAB) substrate kit for peroxidase (Vector laboratories, Burlingame Calif.) was used supplemented with nickel chloride to develop the staining. FIG. 13 shows an osteocalcin-labeled scaffold seeded with Dex+ cells and maintained in culture for 6 weeks. Histological sections of the scaffolds were obtained as following: samples were embedded in Tissue Tek and sectioned vertically at a 6 mm thickness. Cell growth within the scaffolds was also observed from the histological sections. At low magnification, the entire scaffold section could be visualized by LM. In both Dex+ and Dex− cultures, cell coverage was found throughout the entire scaffold structure. Haematoxylin and eosin staining was visible along all the macropores, on the outer surfaces as well as in the middle of the scaffolds. FIGS. 14 and 15 show low magnification of Dex+ and Dex− cultured foams The amount of matrix elaborated on Dex− cultures was far more abundant than on Dex+ cultures, as seen at higher magnification. In Dex+ cultures, only a few cell layers were found lining the pore walls and producing matrix in close apposition to the pore walls, whereas in Dex− cultures, the entire macropore volumes were filled with matrix.

EXAMPLE 7

Seeding Human MarrowCells on Polymer Scaffold

PLGA 75:25 matrices were prepared as described in Example 1. These scaffolds were disinfected in 70% ethanol for 30 min prior to being seeded with human bone marrow stromal cells, from young donors, using protocols and dexamethasone (dex) containing media described in detail by Parker et al (J. of Bone Min. Res., 12(1), S300:F298, 1997).

EXAMPLE 8

Effect of Macropore Size and Interconnectivity on Cell Invasion

Three different scaffold morphologies were created: 1) scaffolds obtained by particulate leaching only, referred to as membranous scaffolds forming part of the prior art and shown in FIGS. 16A, 16B and 16C discussed briefly below, 2) scaffolds obtained by particulate leaching phase inversion using low processing temperatures, as described in Example 1, referred to Intermediate scaffolds and 3) scaffolds obtained by particulate leaching phase inversion using higher processing temperatures, as described in Example 4, referred to as bone-like scaffolds. From each of these three basic processing routes, the three scaffold structures were created with different macropore sizes, so that a total of nine different scaffold structures were obtained. These nine structures are illustrated in FIGS. 16A to 16I.

Figure 16A:
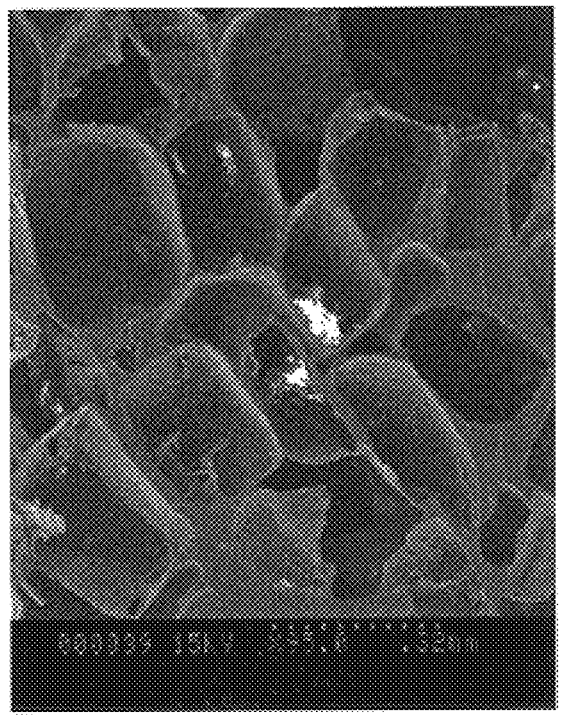
FIG. 16A is a scanning electron micrograph of a prior art PLGA 75/25 membranous scaffold created with particles less than 0.35 mm.
Figure 16B:
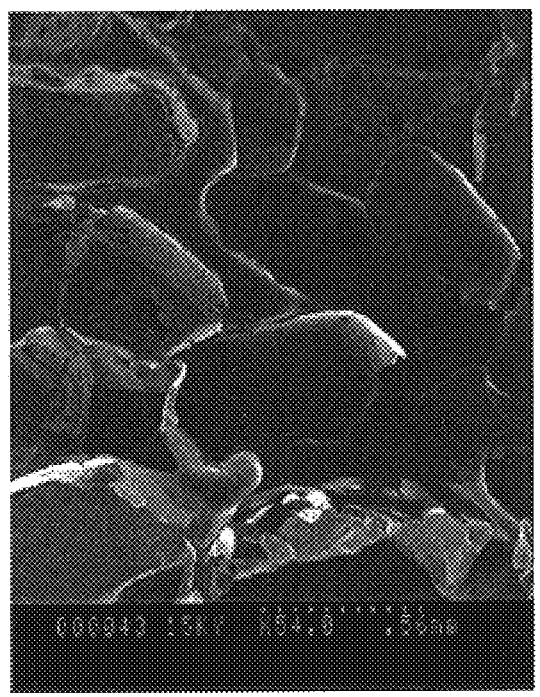
FIG. 16B is a scanning electron micrograph of a prior art PLGA 75/25 membranous scaffold created with particles ranging in size from 0.54 to 0.8 mm.
Figure 16C:
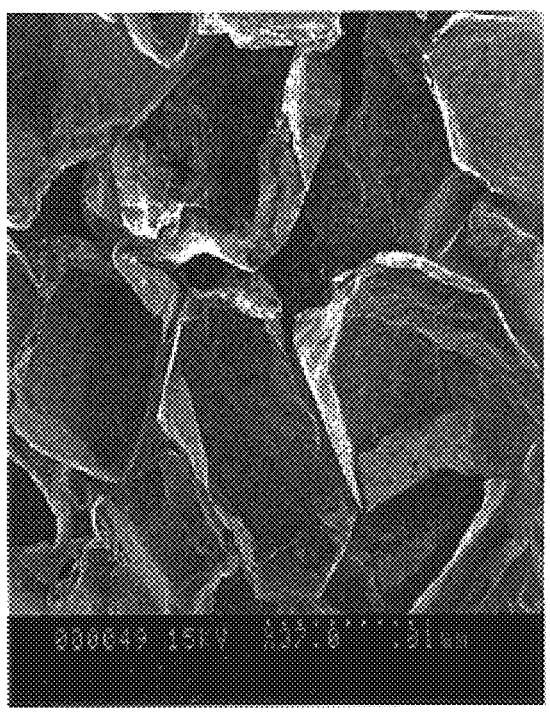
FIG. 16C is a scanning electron micrograph of a prior art PLGA 75/25 membranous scaffold created with particles ranging in size from 0.8 to 2.0 mm.
Figure 16D:
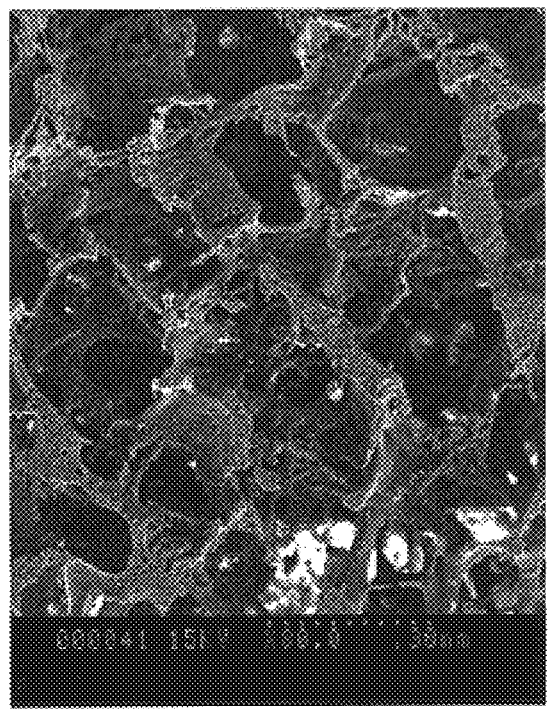
FIG. 16D is a scanning electron micrograph of PLGA 75/25 Intermediate scaffold created with particles less than 0.35 mm.
Figure 16E:
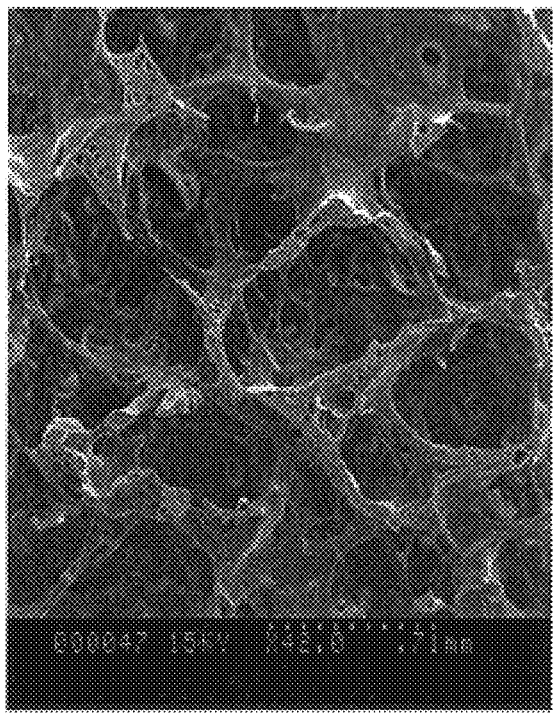
FIG. 16E is a scanning electron micrograph of PLGA 75/25 Intermediate scaffold created with particles ranging in size from 0.54 to 0.8 mm.
Figure 16F:
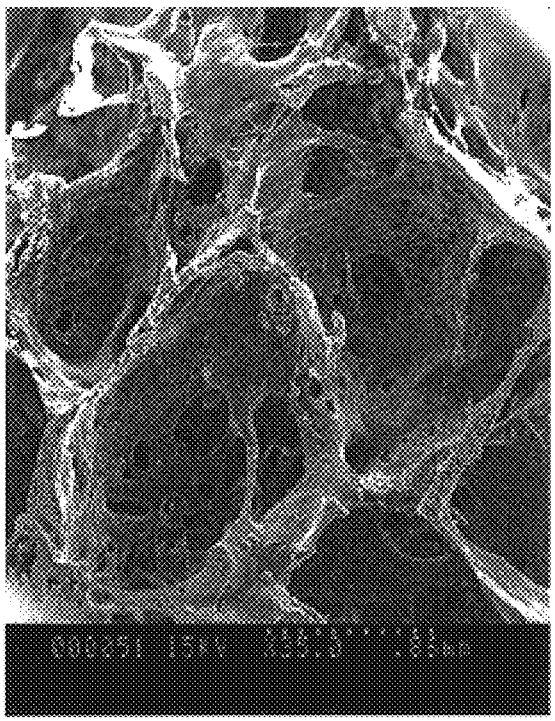
FIG. 16F is a scanning electron micrograph of PLGA 75/25 Intermediate scaffold created with particles ranging in size from 0.8 to 2.0 mm.
Figure 16G:
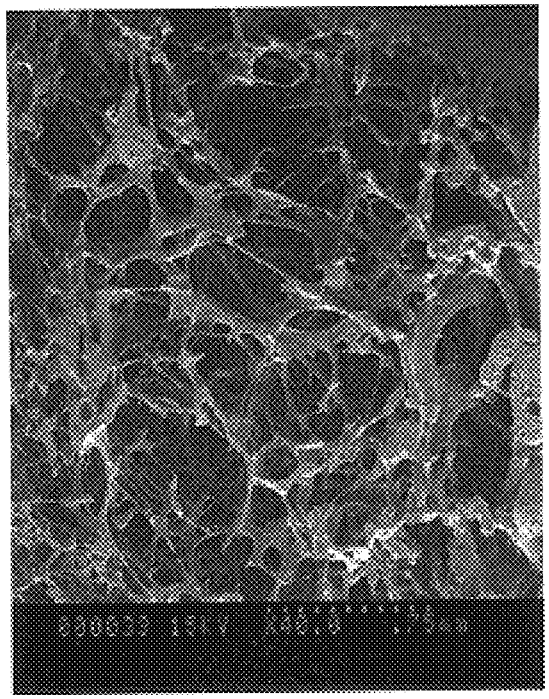
FIG. 16G is a scanning electron micrograph of PLGA 75/25 Bone-like scaffold created with particles less than 0.35 mm.
Figure 16H:
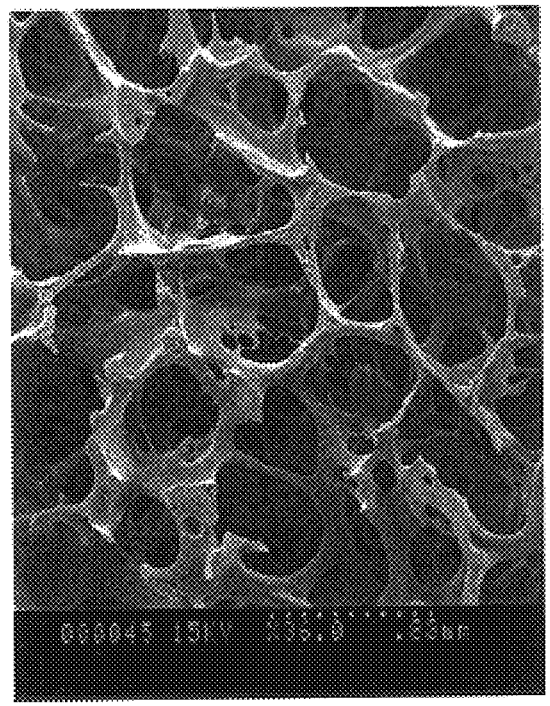
FIG. 16H is a scanning electron micrograph of PLGA 75/25 Bone-like scaffold created with particles ranging in size from 0.54 to 0.8 mm.
Figure 16I:
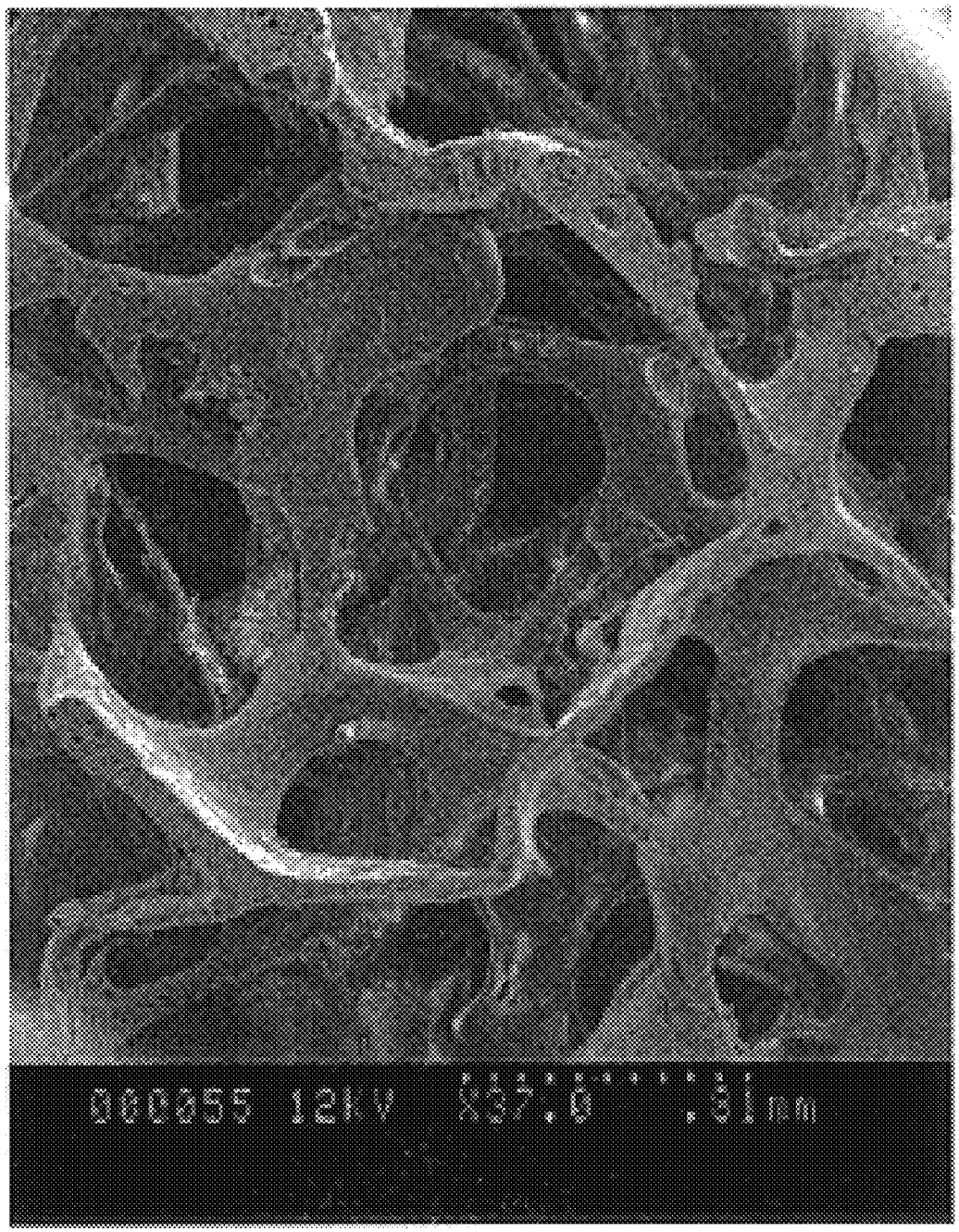
FIG. 16I is a scanning electron micrograph of PLGA 75/25 Bone-like scaffold created with particles ranging in size from 0.8 to 2.0 mm.

Membranous scaffolds were created using a particulate leaching technique only (as described by Mikos et al, in *Biomaterials* 14, 323–330, 1993), see the prior art shown in FIGS. 16A, 16B and 16C. Briefly, a PLGA 75/25 (Birmingham Polymers) solution in chloroform was cast over sieved particles, either 1) NaCl (size<0.35 mm), 2) sucrose crystals (size ranging from 0.54 to 0.8 mm) or 3) glucose crystals (size ranging from 0.8 to 2 mm). The polymer structures were left at room temperature to allow chloroform evaporation, after which the particles were dissolved in ddH$_2$O.

Intermediate and bone-like scaffolds were produced as described in Examples 1 and 4 by extracting the same different particles as described above from the precipitated polymer. Intermediate scaffolds were created at a polymer solution temperature of −20° C. and a non-solvent at room temperature whereas Bone-like scaffolds were produced with a polymer solution temperature at 11° C. and a non-solvent at room temperature. The obtained scaffolds were disinfected in 70% ethanol for 30 min prior to being seeded with cells.

Cell colonization of the scaffolds was confirmed by confocal microscopy, and cell differentiation throughout the scaffold structure was confirmed using the osteocalcin labeling assay described in Example 6. The following results were observed:

TABLE 2

Scaffold Sizes And Cell Colonization Patterns

| | Particle size | | |
|---|---|---|---|
| Scaffold/particle | <0.35 mm | 0.54 to 0.8 mm | 0.8 to 2.0 mm |
| Membranous | | | |
| Macropore size | 0.33 | 0.58 | 1.1 |
| Intercon. Size | 0.01 | 0.09 | 0.9 |
| Cell depth | 0.3 | 0.5 | 1.5 |
| Osteocalcin | Surface | Surface | Surface |
| Intermediate | | | |
| Macropore size | 0.33 | 0.75 | 1.4 |
| Intercon. Size | 0.07 | 0.15 | 0.45 |
| Cell depth | 0.3 | 1.5 | Throughout |
| Osteocalcin | Surface | Surface | Surface |
| Bone-Like | | | |
| Macropore size | 0.35 | 0.7 | 1.8 mm |
| Intercon. Size | 0.2 | 0.35 | 0.65 |
| Cell depth | 1.2 | Throughout | Throughout |
| Osteocalcin | Throughout | Throughout | Throughout |

Cell colonization of the scaffolds, as reported in Table 2, required a minimum interconnection size of 0.35 mm and macropore size of 0.7 mm.

In this Example, membranous scaffolds with macropore size of 1.1 mm were not colonized by cells whereas Bone-like scaffolds with macropore sizes of 0.7 mm were fully colonized by cells. In conclusion, this Example demonstrates that scaffolds obtained by particulate leaching phase inversion technique allowed cell colonization throughout the entire scaffold morphology, whereas previously published scaffold were only colonized by cells within their superficial pore layer.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

We claim:

1. A macroporous polymer scaffold with microporous polymer struts defining interconnected macropores formed by mixing liquid polymer with particles to form a mixture of the liquid polymer and particles, submerging the mixture in a non-solvent for the liquid polymer to precipitate the liquid polymer to produce a solidified mixture, and submerging the solidified mixture into a solvent that dissolves the particles for a time sufficient to dissolve the particles to obtain said macroporous polymer scaffold with microporous polymer struts defining interconnected macropores.

2. A process for synthesizing a macroporous polymer scaffold with microporous polymer struts defining interconnected macropores, comprising the steps of:

mixing liquid polymer with particles to form a mixture of the liquid polymer and particles;

submerging the mixture in a non-solvent for the liquid polymer to precipitate said liquid polymer producing a solidified mixture; and submerging the solidified mixture into a solvent that dissolves the particles for a time sufficient to dissolve the particles to obtain said macroporous polymer scaffold with microporous polymer struts defining interconnected macropores.

3. A process as defined in claim 2, wherein said liquid polymer is formed by dissolving a polymer in a polymer solvent.

4. A process as defined in claim 3, wherein said polymer solvent is dimethylsulfoxide.

5. A process as defined in claim 3, wherein particles have a diameter in the range of about 0.5 to about 3.5 mm.

6. A process as defined in claim 5, wherein said particles have a mean diameter in the range of about 1.0 to about 2.0 mm.

7. A process as defined in claim 2, wherein said particles are selected from the group consisting of polysaccharides, organic salts, inorganic salts, proteins, lipids, and combinations thereof.

8. A process as defined in claim 7, wherein said polysaccharide is glucose.

9. A process as defined in claim 6, wherein said particles are sugar particles.

10. A process as defined in claim 2, additionally comprising the step of modifying the surface of the polymer scaffold.

11. A process as defined in claim 2, wherein the surface of the polymer scaffold is modified using a treatment selected from the group consisting of acid treatment, base treatment, collagen deposition and calcium phosphate deposition.

12. A process as defined in claim 2 including stabilizing said mixture prior to precipitating said liquid polymer.

13. A process as defined in claim 12 wherein said mixture is stabilized by cooling it to a suitable temperature.

14. A process as defined in claim 2, wherein said liquid polymer is formed by heating a polymer to its melting point to liquify said polymer.

15. The process of claim 2 wherein said non-solvent for the polymer is selected from the group consisting of water, alcohol, 1–4 dioxane and aniline.

16. The process of claim 2 wherein said liquid polymer is derived from poly(lactide-co-glycolide).

* * * * *